United States Patent [19]

Gray

[11] Patent Number: 4,917,881
[45] Date of Patent: Apr. 17, 1990

[54] DEHYDRATED GARLIC PREPARATIONS AND BUFFER COMPOUNDS TO ALLEVIATE DIGESTIVELY INDUCED AFTEREFFECTS

[76] Inventor: Daniel S. Gray, 37 Albourne St., South River, N.J. 08882

[21] Appl. No.: 164,191

[22] Filed: Mar. 4, 1988

[51] Int. Cl.⁴ .................. A61K 35/78; A61K 33/32
[52] U.S. Cl. .................................. 424/10; 424/643; 424/195.1
[58] Field of Search .............. 424/145, 195.1, 10, 424/643

[56] References Cited

U.S. PATENT DOCUMENTS 2,365,245  12/1944  Bruce .......................... 424/145
4,410,446  10/1983  Cheny et al. ................. 424/145

FOREIGN PATENT DOCUMENTS 259157  12/1985  Japan .

*Primary Examiner*—Douglas W. Robinson
*Assistant Examiner*—Raymond J. Henley, III
*Attorney, Agent, or Firm*—Arthur L. Plevy

[57] ABSTRACT

There is disclosed a unique composition which essentially comprises a granule or cell or garlic having adhered thereto a suitable amount of zinc oxide. The zinc oxide acts as a buffer to alleviate the unpleasant aftereffects which are cused by the ingestion or consumption of garlic. In this manner zinc oxide functions to digestively avoid such unpleasant aftereffects associated with the ingestion or consumption of garlic.

8 Claims, 1 Drawing Sheet

DEHYDRATED GARLIC PREPARATIONS AND BUFFER COMPOUNDS TO ALLEVIATE DIGESTIVELY INDUCED AFTEREFFECTS

BACKGROUND OF THE INVENTION

This invention relates to a garlic product, having zinc oxide attached thereto and more particularly to a dehydrated garlic powder having bonded or secured thereto zinc oxide to alleviate digestively induced aftereffects.

As is well known, the amount of garlic sold increases each year as many people enjoy the taste and flavor of garlic. As is also well known, garlic produces breath odors as well as gastric discomfort. These adverse effects are due to the odor of the garlic and furthermore when garlic is ingested it produces sulphur gases when combined with the various stomach and digestive fluids. These gases cause discomfort and emanate in characteristic odors which are often extremely annoying and offensive.

It has been determined that by utilizing dehydrated garlic preparations in conjunction with a suitable buffer compound one can alleviate digestively induced aftereffects. Hence, according to the present invention, one employs a suitable amount of zinc oxide which is secured to a garlic cell or otherwise infused into the cell to thereby operate to alleviate the unpleasant aftereffects which are caused by the consumption of garlic. The resultant preparations operate to control the "after odors" due to garlic ingestion to substantially reduce such digestive odors. It is believed that the zinc oxide actively combines with digestive fluids which are generated due to the ingestion of garlic to render resultant obnoxious gases inert and to therefore prevent the gastric disturbances caused by the ingestion of garlic.

It is therefore an object of the present invention to produce a garlic product which eliminates offensive after effects due to the digestion of the garlic.

It is a further object of the present invention to provide a product which consists of granules of garlic having secured or otherwise associated therewith particles of zinc oxide to produce a garlic preparation having all the qualities and taste of garlic while substantially reducing the above-noted after effects.

BRIEF DESCRIPTION OF PREFERRED EMBODIMENT

A garlic product comprising a granule of garlic having coupled thereto an effective amount of zinc oxide operative to alleviate the unpleasant aftereffects caused by the consumption of garlic.

DETAILED DESCRIPTION OF INVENTION

Figure 1:
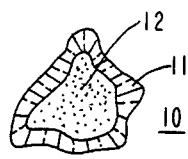
FIG. 1 is a cross-sectional view of a typical garlic cell or garlic granule.

Referring to FIG. 1 there is shown the granule or cell of garlic. Essentially, although the following will be discussed on a cell basis, it is understood that due to the nature of garlic one can implement the present invention by utilizing a plurality of cells or a module or granule of garlic, such as a dehydrated garlic powder. It is the object and intent of this invention to bind to a predetermined amount of garlic, such as a granule or a cell of garlic, a predetermined amount of zinc oxide to avoid aftereffects due to digestive processes.

A typical cell of garlic contains an internal plasma 12 which constitutes the vegetable cell matter contained in the garlic. As is well known garlic is a typical plant related to onion and has a bulb with a strong distinctive odor and flavor. The bulb of this plant is divisible into separate cloves and is conventionally used as a seasoning. As shown in FIG. 1 the module or granule or cell of garlic 10 contains a cell wall 11 with an internal plasma 12.

Figure 2:
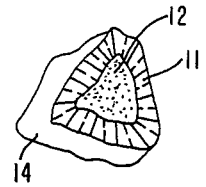
FIG. 2 is a cross-sectional view of a garlic cell having adhered thereto a suitable buffer according to this invention.

Shown in FIG. 2 is a module 14 which is bound to the cell wall of the garlic and which consists of zinc oxide. Zinc oxide and the production of zinc oxide is well known. Zinc oxide, sometimes referred to as flowers of zinc or philosophers wool or zinc white, has a molecular weight of 81.38 and contains 80.34% of zinc and 19.66% of oxygen. Zinc oxide occurs as the mineral zincite. It is prepared by vaporization of metallic zinc and oxidation of the vapors with preheated air and also from franklinite or from zinc sulfide. See *Faith, Keys and Clark Industrial Chemicals* published by Wiley, New York, 4th Edition, 1975, pages 882–888. Zinc oxide is used in medicinal grades which contain 99.5% or more of pure zinc oxide. Zinc oxide, in relatively small amounts, is non-toxic and, as indicated, will operate to react with digestive fluids produced during the digestive process and hence substantially reduce the unpleasant aftereffects or after odors due to the generation of sulphur gases based on the ingestion of garlic.

As indicated in FIG. 2, zinc oxide can be directly secured to a granule or module of garlic by adhering to the cell wall 11 of the garlic or by actually encapsulating a portion or a granule of garlic. As indicated, the prior art is cognizant of many techniques for the fabrication or formation of zinc oxide, as one can produce highly porous and sub-micron size particles of zinc oxide.

In this manner many prior art patents, such as U.S. Pat. No. 4,410,446, depict processes which can be utilized to secure zinc oxide particles to granules or cells of garlic. In that patent there is described a stable fluid zinc containing dispersion and preparations for the dispersion by high temperature decomposition of zinc acetate to zinc oxide in a dispersant containing fluid. The dispersant fluid being stable at the temperature of composition. By utilizing such techniques one can therefore assure the adhesion of the zinc oxide particles to the garlic granules which would be included in the solution during the preparation of zinc oxide.

One can also suspend zinc particles in a water-dry emulsion and then add particles of garlic or dehydrated garlic powder to the emulsion and then vacuum dry the entire contents to produce adherence of the zinc particles to the garlic powder. One can also employ techniques whereby the granules of garlic are essentially treated in such a manner that they are coated with the zinc oxide by the use of a vegetable or other type of digestible glue. This process can be implemented by means of selective screens or other filtration means to enable zinc oxide in sufficient amounts to adhere to granules of garlic.

Figure 3:
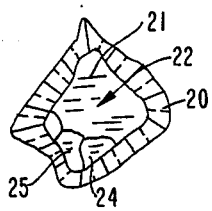
FIG. 3 is an alternate embodiment of a garlic cell having inserted within the plasma of the cell a suitable amount of a garlic oil concentrate and zinc oxide.

FIG. 3 describes a preferred embodiment whereby there is shown a cell of garlic having a cell wall 20 and an internal plasma 22. In the technique to be described, a sufficient amount of zinc oxide actually permeates or diffuses through the cell wall 20 as well as a highly concentrated source of garlic, such as a garlic oil concentrate. In this manner the module shown in FIG. 3 contains inside the plasma 22 of the cell a portion 24, which is of zinc oxide, and a portion 25, which is a garlic oil concentrate. While FIG. 3 shows these as discrete sections or areas, it is immediately ascertained that both the garlic oil concentrate, as well as the zinc oxide, are relatively uniformly diffused throughout the plasma 22 of the cell.

Figure 4:
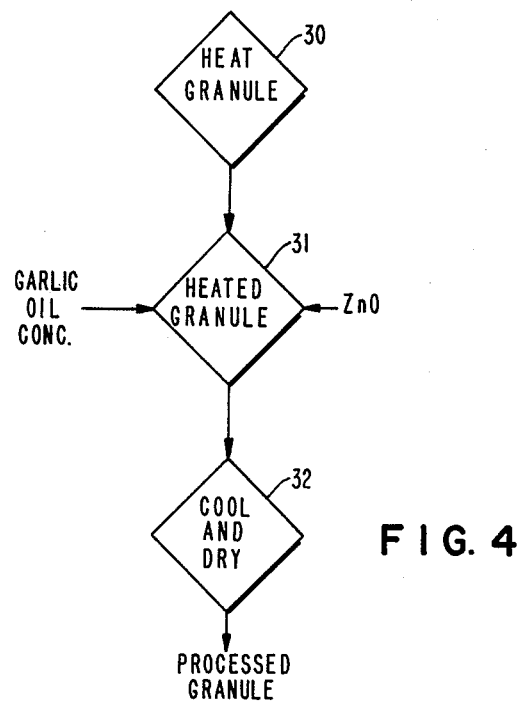
FIG. 4 is a block diagram showing one process for coupling zinc oxide and garlic oil concentrate to a typical garlic cell.

Referring to FIG. 4, the process and method will be described. As will be explained, a typical plant cell wall, as 20, is fabricated from cellulose. Cellulose is found almost exclusively in plants and accounts for abut 30% of all vegetable matter. Cellulose is the principal substance of which the walls of vegetable cells are constructed.

FIG. 4 shows a method of infusing zinc oxide into garlic to obtain the configuration, as for example depicted in FIG. 3. As shown in FIG. 4, powdered or dehydrated garlic powder granules are subjected to heat. As is well known, cellulose is a white, solid, odorless and tasteless material which is insoluble in cold or hot water and is chemically non-reactive except when treated with strongly corrosive materials. In any event, if cellulose is heated at temperatures less than 260° C., the cell wall begins to stretch allowing permeation of the cell wall. In this manner the garlic granules are heated, as indicated by FIG. 4 by reference numeral 30. This heating can take place in water or any other solution. A suitable technique is to vacuum heat the granules in a vacuum vessel with about 2% moisture at a temperature of 65° C. The heating opens the cell wall 20. The amount of zinc oxide used is about 7-15 milligrams per 5 grams of garlic. The concentrate may be between 100 milligrams to 1 gram per 5 grams of garlic. A garlic oil concentrate is then diffused into the heated cell. The garlic oil concentrate is obtained by pressing cloves of garlic to obtain a liquid. This liquid is then mixed with the heated granules. At the same time zinc oxide is introduced and the heated mixture is stirred. What occurs is that the cell wall, due to the heating, begins to decompose allowing materials to permeate within the cell wall. The entire mixture is then cooled resulting in granules or modules of garlic having enclosed within the cell wall garlic oil concentrate as well as a suitable amount of zinc oxide. The added zinc oxide, as indicated above, operates to prevent after odors. Both the zinc oxide and the garlic oil concentrate are actually directed through the cell wall by means of the heating process and the stirring or agitation procedure. In this manner one obtains a concentrate of zinc oxide within a garlic cell wall plus the addition of the garlic oil concentrate to further enhance the flavor of the final product.

As indicated above, the zinc oxide serves to act as a buffer whereby the zinc oxide combines with digestive fluids as HCL in the stomach to prevent sulphur gases which are normally generated during the digestive process. In this manner the zinc operates to alleviate the unpleasant aftereffects which are caused by the consumption of garlic. Thus the zinc oxide functions in combination with the garlic to digestively avoid such aftereffects.

As one can ascertain from the above, there are many ways of securing zinc oxide to a granule or particle or cell of garlic and such techniques should be apparent to those skilled in the art and are encompassed within the scope and breadth of the claims as appended hereto.

What is claimed is:

1. A garlic product comprising a granule of garlic including an effective amount of zinc oxide which amount is between 7-15 milligrams per 5 grams of garlic granules operative to alleviate the unpleasant aftereffects caused by the consumption of garlic.

2. The garlic product according to claim 1 wherein said zinc oxide is attached to the cell wall of said garlic granule.

3. The garlic product according to claim 1 wherein said zinc oxide is placed within the plasma of the cells of said garlic granule.

4. The garlic product according to claim 1 wherein said garlic granule is a granule of dehydrated garlic powder.

5. The garlic product according to claim 1 further including a garlic oil concentrate formed by pressing garlic cloves located within the plasma of the cells of said garlic granule to further enhance the flavor or said granule.

6. A process for producing a garlic product comprising the steps of:
   heating garlic granules in vacuum to a temperature below 260° C. sufficient to allow permeation of the cell wall;
   adding a garlic oil concentrate to said heated granules to allow said concentrate to diffuse through said wall into said cell plasma, said concentrate formed by pressing garlic cloves and adding between 100 milligrams to 1 gram of concentrate per 5 grams of garlic;
   adding zinc oxide to said heated granules to allow a sufficient amount of said oxide to diffuse into said cell wall, adding between 7-15 milligrams of zinc oxide to 5 grams of garlic granules;
   cooling said processed granules to attain granules having a garlic oil concentrate and zinc oxide located in each cell, said zinc oxide of an effective amount to alleviate the unpleasant aftereffects due to the consumption of garlic.

7. The process according to claim 6 wherein the step of heating said granules is in water at temperatures sufficient to allow cell wall permeation.

8. The process according to claim 6 wherein said garlic granules are granules of dehydrated garlic powder.

* * * * *